(12) United States Patent
Spenser et al.

(10) Patent No.: US 9,108,025 B2
(45) Date of Patent: Aug. 18, 2015

(54) APPARATUS AND METHOD FOR ANCHORING AN ELONGATED OBJECT IN BODY LUMENS

(75) Inventors: Benjamin Spenser, Hof Karmel (IL); Omry Nachum Ben-Esra, Tel Aviv (IL)

(73) Assignee: Gardia Medical Ltd., Caesarea (IL)

( * ) Notice: Subject to any disclaimer, the term of this patent is extended or adjusted under 35 U.S.C. 154(b) by 880 days.

(21) Appl. No.: 13/123,075

(22) PCT Filed: Oct. 8, 2009

(86) PCT No.: PCT/IB2009/054427
§ 371 (c)(1),
(2), (4) Date: May 26, 2011

(87) PCT Pub. No.: WO2010/041216
PCT Pub. Date: Apr. 15, 2010

(65) Prior Publication Data
US 2011/0224769 A1    Sep. 15, 2011

Related U.S. Application Data (60) Provisional application No. 61/104,120, filed on Oct. 9, 2008.

(51) Int. Cl.
*A61N 1/05* (2006.01)
*A61M 25/04* (2006.01)
*A61M 25/01* (2006.01)

(52) U.S. Cl.
CPC ........... *A61M 25/04* (2013.01); *A61M 25/0147* (2013.01); *A61M 25/0158* (2013.01); *A61M 2025/0161* (2013.01); *A61M 2025/0163* (2013.01); *A61N 1/0558* (2013.01)

(58) Field of Classification Search
CPC ....... A61N 1/056; A61N 1/057; A61B 5/042; A61B 2018/00273; A61B 2018/00279; A61B 2018/00345; A61F 2/013
See application file for complete search history.

(56) References Cited

U.S. PATENT DOCUMENTS

| | | |
|---|---|---|
| 2,498,692 A | 2/1950 | Mains |
| 4,826,087 A | 5/1989 | Chinery |
| 5,378,236 A | 1/1995 | Seifert |
| 5,522,880 A | 6/1996 | Barone |
| 5,674,197 A | 10/1997 | van Muiden et al. |
| 5,925,054 A | 7/1999 | Taylor et al. |
| 6,126,649 A | 10/2000 | Van Tassel et al. |
| 6,669,707 B1 | 12/2003 | Swanstrom et al. |
| 6,986,778 B2 | 1/2006 | Zadno-Azizi |
| 7,819,844 B2 * | 10/2010 | Spenser et al. ............ 604/165.02 |
| 2005/0080472 A1 * | 4/2005 | Atkinson et al. ............... 607/126 |
| 2007/0162071 A1 * | 7/2007 | Burkett et al. ................. 606/200 |

* cited by examiner

*Primary Examiner* — Carl H Layno
*Assistant Examiner* — Erin Piateski
(74) *Attorney, Agent, or Firm* — Pearl Cohen Zedek Latzer Baratz LLP (57) ABSTRACT

An apparatus and method for anchoring an elongated object, for example a wire, in tubular body vessel, such as arteries, veins, the colon, bile ducts, etc. are disclosed. The wire may be a catheter, a guide wire, a tube or an electrical lead. In one embodiment, a fixation device is advanced over the wire and, upon external actuation, either deforms the wire or deploys an anchoring mechanism so as to secure the wire against the vessel wall. The anchoring mechanism can be easily removed from the vessel even in the presence of vessel occlusion. In another embodiment, a wire tensioned between two locations on a distal section of the wire deforms the wire and urges the wire into wall apposition.

4 Claims, 9 Drawing Sheets

APPARATUS AND METHOD FOR ANCHORING AN ELONGATED OBJECT IN BODY LUMENS

CROSS-REFERENCES TO RELATED APPLICATIONS

This application is the U.S. National Stage of International Application No. PCT/IB2009/054427, filed Oct. 8, 2009, which designated the United States and has been published as International Publication No. WO 2010/041216, and which claims the priority of U.S. Provisional Patent Application, Ser. No. 61/104,120, filed Oct. 9, 2008, pursuant to 35 U.S.C. 119(a)-(d).

The following US patent applications are incorporated herein by reference in their entirety: US 2009/0105653 A1, titled "Guidewire Stop", filed Oct. 17, 2007, and US 2010/0204725 A1, titled "Guidewire Stop", filed Apr. 27, 2010.

FIELD OF THE INVENTION

The invention relates to an apparatus and method for anchoring an elongated object in tubular body passages, such as arteries, veins, the colon, bile ducts, etc. The wire may be a catheter, a guide wire, a tube or an electrical lead.

BACKGROUND OF THE INVENTION

Wires, more particularly guidewires, are used in medical procedures to guide medical instruments and treatment devices, such as catheters, stents, embolic protection devices (EPD), etc., into and through small body lumens. For example, an EPD filter is typically inserted over or together with a guidewire using a delivery catheter. Following the treatment procedure, the filter is collapsed and removed from the body over the guidewire or together with the guidewire. Additional treatment devices, such as balloons and stents, can be inserted and removed via the same guidewire.

The distal end of the guidewire is in most situations unsupported in the lumen, so that insertion of the medical instruments and treatment devices may cause unwanted movement of the guidewire and even dislodgement of the guidewire. This problem may be exacerbated when heavier devices are advanced over the guidewire.

Other types of wires used in medical procedures are electrical leads for electrical stimulation therapy to treat a variety of symptoms or conditions such as cardiac arrhythmias, chronic pain, tremor, Parkinson's disease, multiple sclerosis, spinal cord injury, cerebral palsy, amyotrophic lateral sclerosis, dystonia, torticollis, epilepsy, pelvic floor disorders, or gastroparesis. One or more stimulation leads are typically percutaneously or surgically implanted in a patient on a temporary or permanent basis, with at least one stimulation electrode being positioned proximate to a target stimulation site. The target stimulation site may be, for example, a spinal cord, pelvic nerve, pudendal nerve, stomach, muscle, or within a brain, the heart or another organ of a patient. For example, the electrodes may deliver stimuli for cardiac resynchronization therapy (CRT).

In most cases, the electric leads are attached to the target organ, such as a cardiac vein or artery, by an anchoring a component located at the tip of the lead in form of, for example, a threaded fixation structure or extendable fixation devices located near the tip, an inflatable balloon, etc. While fixation of pacemaker leads in the right ventricle is successful in most cases, stable fixation within certain vasculature in the human body, such as the coronary sinus for CRT applications, have proven more difficult. Improper lead implantation can sometimes occur during deployment, due to tortuous venous anatomy. Occasionally, lead implantation results in complications, such as coronary sinus dissection or phrenic nerve stimulation.

Lead migration sometimes occurs subsequent to implantation, due to inadequate anchoring mechanisms. With the introduction of biventricular pacing, leads also had to be permanently placed in the cardiac veins, so that fixating electrodes within the vein has become an important clinical problem. The thin wall of the vein does not support the use of screws for fixation, and the smooth vascular wall does not readily support the use of mechanical friction fixating devices. Currently, several methods have been reported to fixate electrical leads in a cardiac vein; however, lead migration still remains a significant clinical problem.

With current technologies, the fixation structure or fixation devices are permanently attached to or incorporated in the electrical lead and in most cases form the tip of the lead. This arrangement makes it impossible to later move the tip of the lead relative to the fixation structure, for example, to improve coupling between the lead tip and the treatment site.

Accordingly, there is a need for improved lead fixation in a body lumen, wherein positioning of the electrical lead or the guidewire is independent of placement of the fixation structure, and wherein possibilities exist for later repositioning the tip of the wire or guidewire relative to the fixation structure, without moving the fixation structure inside the body lumen.

SUMMARY OF THE INVENTION

In general, the invention is directed toward an implantable medical elongated member, such as a guidewire or an electrical lead, which can be inserted into a body lumen and which can be used to guide a fixation device to a location in the body lumen, wherein the fixation device is held in place inside the body lumen, for example, mechanically by friction. In some embodiments, the guidewire or electrical lead wire can then be also affixed to the fixation device, either releasably or permanently. In some embodiments, the fixation device is in form of a coil or can be shaped into a coil or another deformed or tortuous structure, which can be delivered by a catheter. The coiled shape can be made, for example, of a shape memory metal, such as Nitinol.

Although the examples described in the context of this application are mainly directed to pacing leads, these can apply to any elongated object such as catheter, guide wire, tube, etc.

In one exemplary embodiment, the fixation device is tubular and when activated is deformed into a spiral, thus forcing the wire, such as the pacing wire or lead into a helical shape at that location. The formed spiral is in apposition to the vein wall and fixes the lead in place.

In another embodiment, the tubular fixation device may include an activation wire that is pulled distally (outside of the body) to activate the fixation device, thereby allowing the fixation device to deform into the tortuous shape for vessel wall apposition.

In some embodiments of the current invention, the fixation device may include an expanding member, for example made of a wire, which engages the vein wall once activated. In some embodiments, the fixation device is an expanding member, for example a balloon, that when inflated is large enough to engage opposing walls of the cecum. It will be understood that the fixation device need not be a single element, but that more than one element can be employed, which allow free passage of the guidewire and other equipment through the fixation device. In yet another embodiment, an inducer apparatus and method, similar to a catheter, are provided for lead retrieval.

These and other features and advantages of the present invention will become more readily appreciated from the detailed description of the invention that follows.

BRIEF DESCRIPTION OF THE DRAWINGS

The following figures depict certain illustrative embodiments of the invention in which like reference numerals refer to like elements. These depicted embodiments are to be understood as illustrative of the invention and not as limiting in any way.

DETAILED DESCRIPTION OF THE INVENTION

The exemplary embodiments of the invention described below are directed to securing a lead, such as a pacing lead in a coronary vessel. This can be attained by forcing the pacing lead, once introduced into the vessel, into vessel wall apposition by external actuation, for example, from the proximal end of an insertion catheter. This can be attained by advancing a fixation device with a locking mechanism over the pacing lead, using the pacing lead essentially as a guidewire, and then actuating the fixation device externally from the proximal end of an insertion catheter. Additionally, a wire lock can be employed to lock the fixation device in place on the pacing lead.

Figure 1:
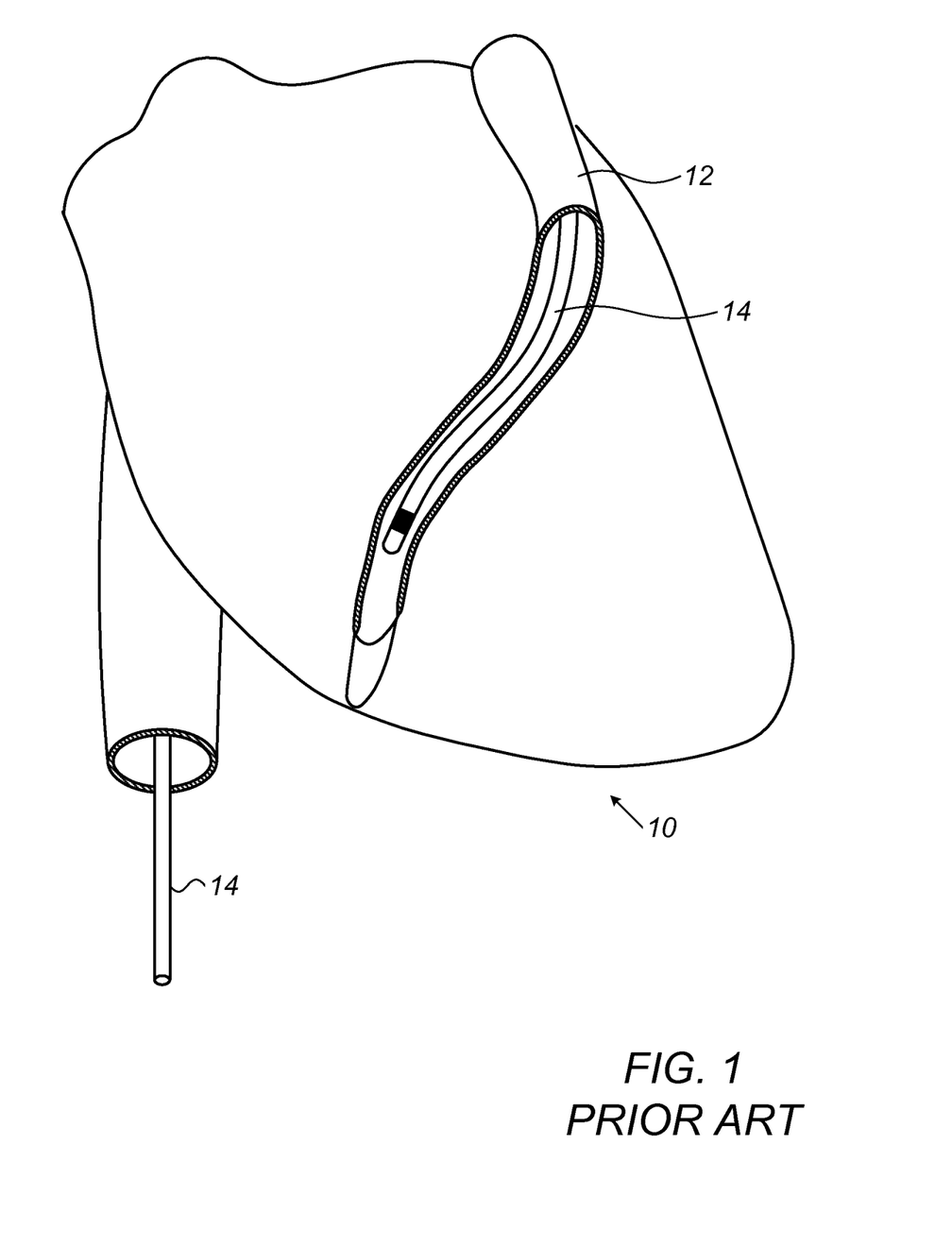
FIG. 1 shows a heart with the coronary sinus with a pacing lead in partial cross-section.

Turning now to the appended Figures, FIG. 1 shows a view of the heart 10, with the coronary sinus 12 shown in partial cross-section. A straight section of a pacing lead 14 can be seen inside the vessel. As can be seen, the pacing lead 14 is not anchored in the vessel and can be easily dislodged.

Figure 2:
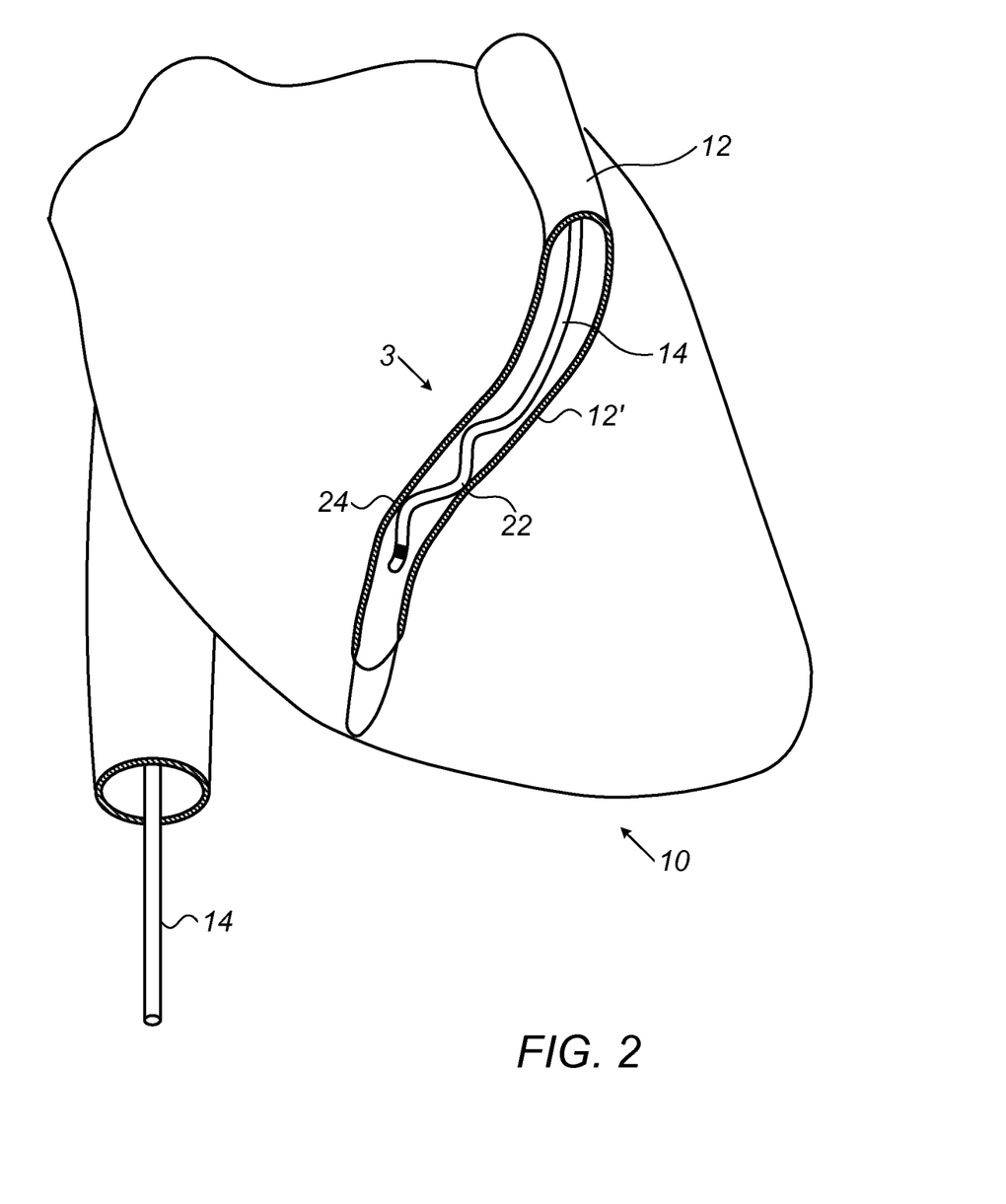
FIG. 2 shows the pacing lead of FIG. 1 re-shaped to a two-dimensional deformed pattern.
Figure 3:
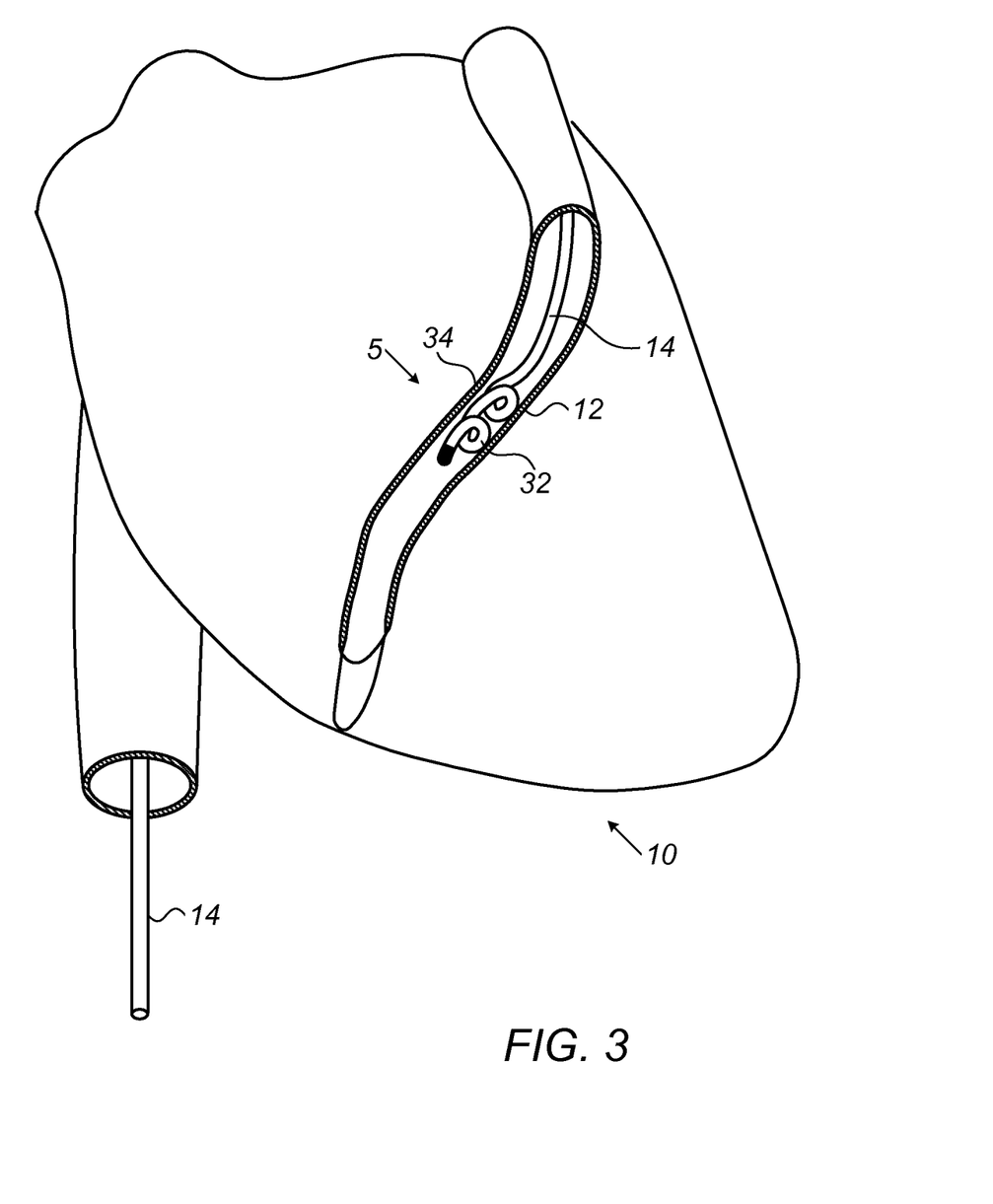
FIG. 3 shows the pacing lead of FIG. 1 re-shaped to a three-dimensional helical pattern.

One approach for anchoring the pacing lead in the coronary sinus 12 is to deform the pacing lead 14 into a deformed shape, either two-dimensionally in a meander shape 3, as shown in FIG. 2, or three-dimensionally in form of a helical shape 5, as shown in FIG. 3. This deformation may be performed with a separate fixation device or fixation attachment. Examples of such fixation devices will be described below in conjunction with FIGS. 4, 6 and 7. The resulting deformation, illustrated schematically in FIG. 2, will bring sections 22 and 24 of the deformed fixation device into apposition with the vessel wall 12', thereby anchoring the pacing lead 14 through friction.

Figure 4:
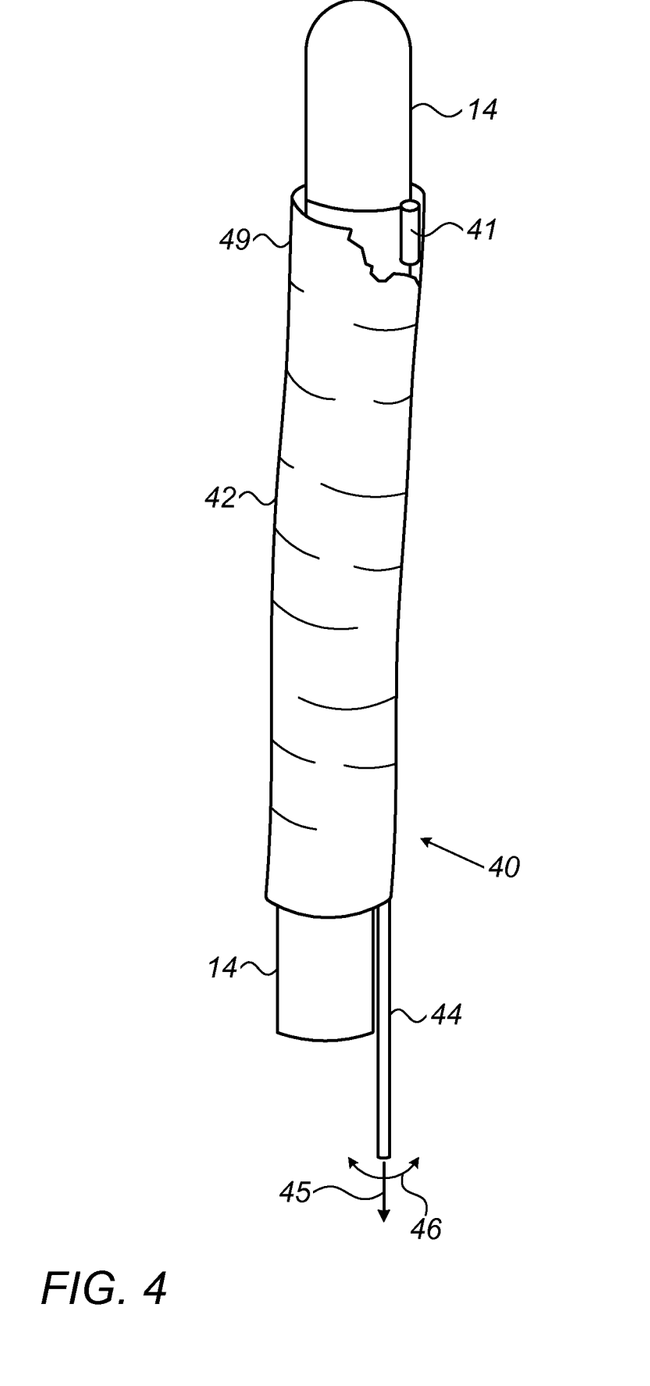
FIG. 4 shows a mechanism configured for reshaping the fixation device inside a vessel.
Figure 5:
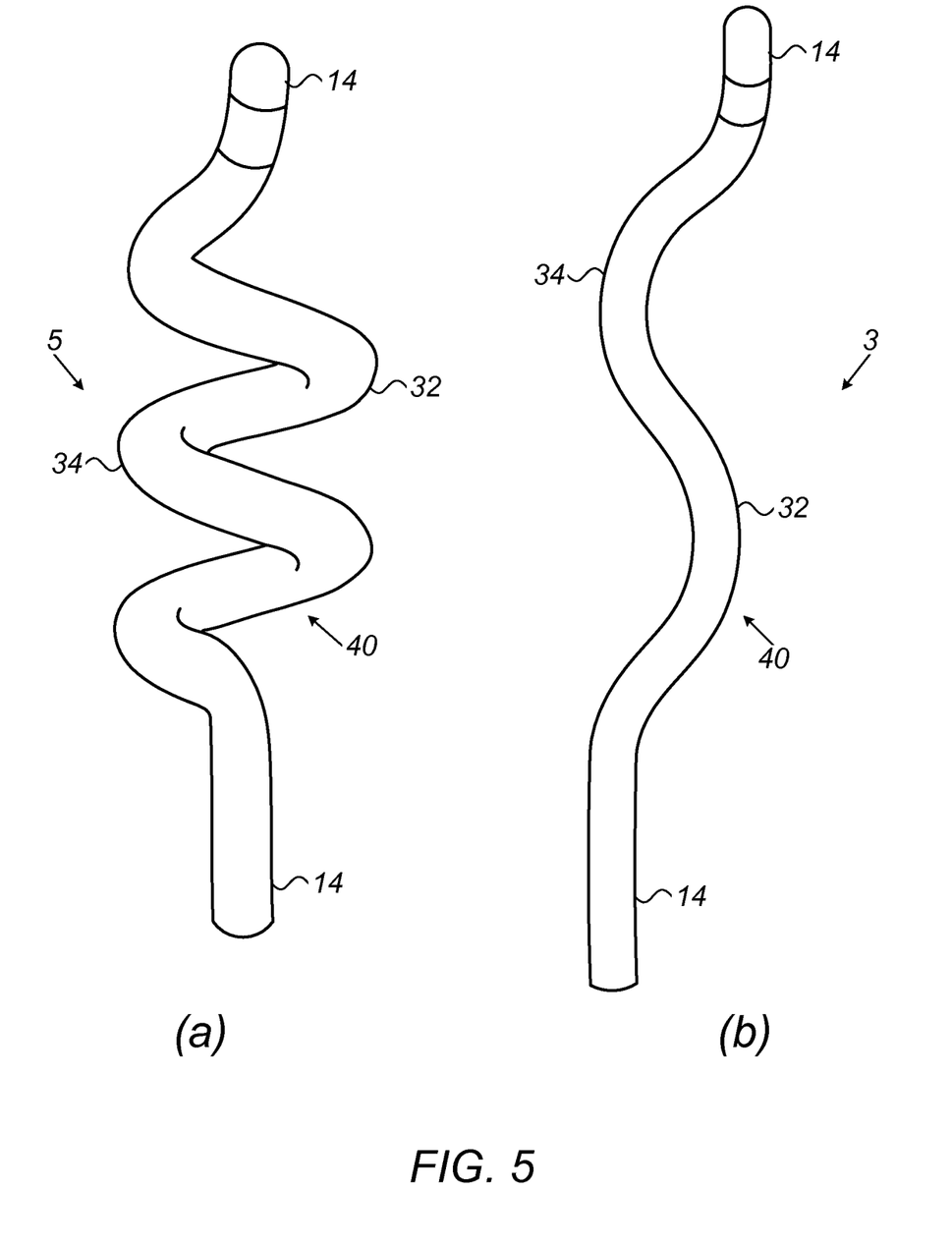
FIG. 5 shows the two-dimensional pattern (a) and three-dimensional (b) pacing lead of FIGS. 2 and 3 in more detail.

FIG. 4 illustrates an exemplary embodiment of a fixation device 40 which includes structural attributes and a mechanism for deforming an originally straight fixation device 40 into the meander (FIG. 2) or helical shape (FIG. 3). The fixation device 40 is here formed as a hollow shaft receiving the pacing lead 14 and has a pattern 42 formed in the shaft wall, with an exemplary pattern including, for example, pre-cut grooves or a section with decreased wall thickness to provide weak links or rated break points. The fixation device 40 may be deployed at the implant site by a delivery catheter (not shown) similar to the delivery catheter 75 described below in conjunction with the discussion of FIG. 7. A pulling wire 44 is attached at 41 to the distal end 49 of the fixation device 40. When the wire 44 is pulled downward in the direction of arrow 44, i.e., towards the proximal end of the pacing lead 14, the location of the proximal end of the hollow fixation device 40 is fixed by the delivery catheter, so that fixation device 40 will collapse to a predetermined shape defined by the pattern 42 and deform the pacing lead 14, as shown in more detail in FIG. 5a (corresponding to the two-dimensional meander shape of FIG. 2) and FIG. 5b (corresponding to the three-dimensional meander shape of FIG. 3). It will be understood that the depicted shapes of the deformation are only examples, and that other deformed configurations can be contemplated as long as these configurations securely anchor the pacing lead 14 in a vessel 12. The wire 44 can be detached from the fixation device 40 by incorporating a rated breakpoint at a location along the wire, for example, near the distal attachment point 41. The rated breakpoint can be constructed similar to breakpoints described in copending applications WO 2009/050599 and WO 2009/050600, both titled "Guidewire Stop." The wire 44 can be severed either by pulling or twisting.

Figure 6:
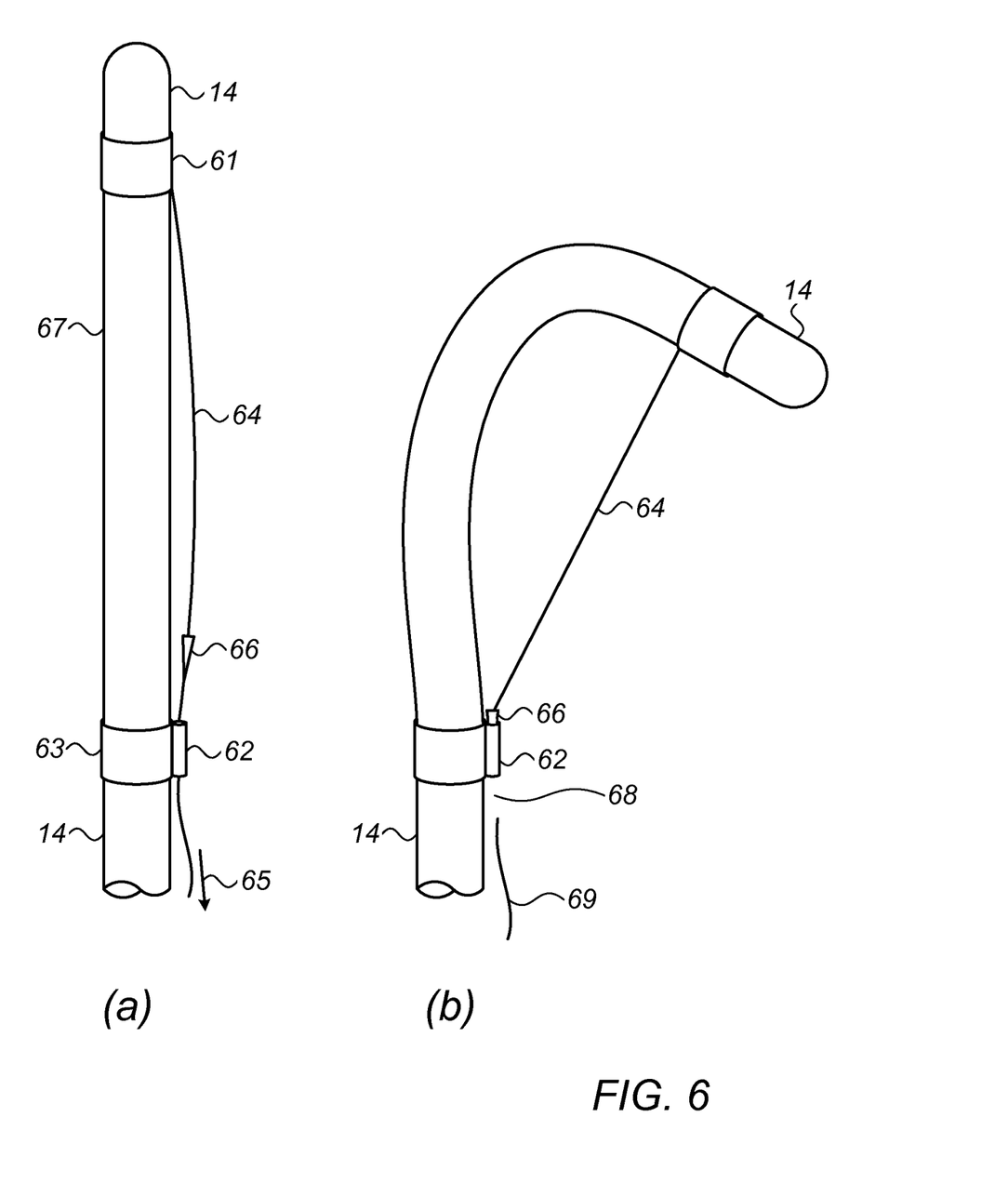
FIG. 6 shows another mechanism configured for reshaping the fixation device inside a vessel.

In another exemplary embodiment illustrated in FIG. 6, an originally straight section of a pacing lead 14 (FIG. 6a) can be shaped into a deformed pattern adapted for securement in a vessel 12 by securing a pulling wire 64 to the distal portion 67 of the pacing lead 14 at two locations 61 and 62. The pulling wire 64 is fixedly attached near the distal end 61 of pacing lead 14; the pulling wire 14 is guided through an opening 62 of a shaft ring 63 secured to the pacing lead 14 proximal of the distal end 61 for longitudinal movement relative to the shaft ring 63 and hence relative to the pacing lead 14. A securement device 66, illustrated as an exemplary wedge 66, is attached to the pulling wire 64 at a location between the distal end 61 and the shaft ring 63. It will be understood that the securement device 66 may have other shapes, such as a conical shape or shapes similar to those described in copending applications WO 2009/050599 and WO 2009/050600. When the pulling wire 64 is pulled in the direction of arrow 65, the distal portion 67 of the pacing lead 14 bends until the securement device or wedge 66 engages with and locks inside the opening 62 of shaft ring 63. Alternatively, instead of providing a separate opening 62, the wedge 66 may lock directly between the shaft ring 63 and the distal portion 67 of the pacing lead 14. As indicated in FIG. 6b, the pulling wire 64 may be designed to tear at the rated break point 68 under the pulling force following locking of wedge 66 or by a rotation of the pulling wire 64. The curved section 64 of the pacing lead 14 is now in apposition with the vessel wall (not shown), securing the pacing lead inside the vessel 12.

Figure 7:
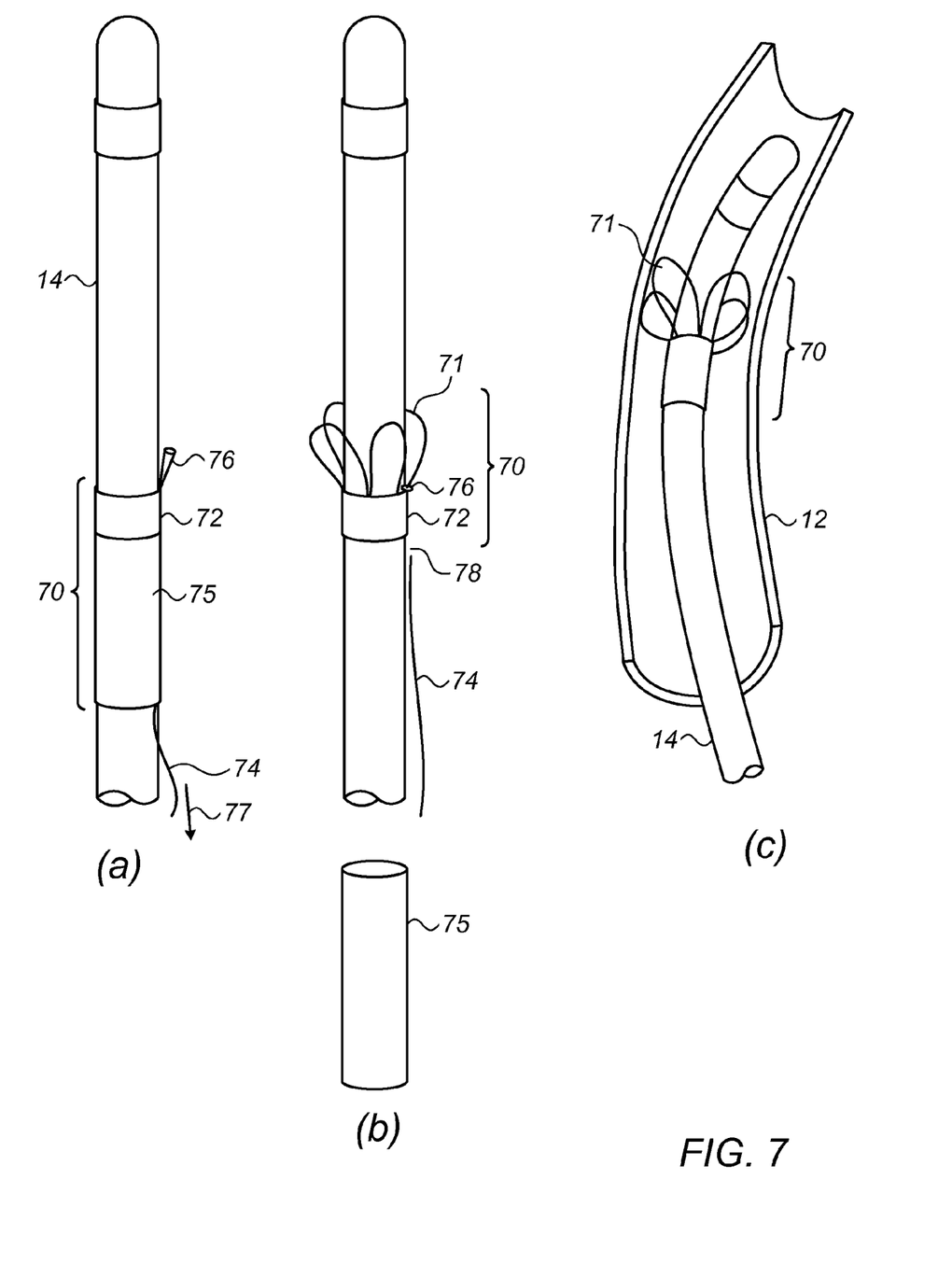
FIG. 7 shows a different anchoring mechanism for a pacing lead in a vessel.

Another exemplary embodiment illustrated in FIGS. 7a to 7c employs a different type of anchoring mechanism 70 for improving securement of a pacing lead 14 in a blood vessel 12 (not shown in FIG. 7). The anchoring mechanism 70 is here embodied as a plurality of wires loops 71 protruding from a shaft ring 72. The anchoring mechanism 70 can be advanced into the vessel over a conventional pacing lead 25, operating much like a guidewire, for example, by using an insertion catheter 75. The shaft ring 72 can be locked in place on the pacing lead 14 with a guidewire stop of a type described in copending applications WO 2009/050599 and WO 2009/050600, which may be implemented as a wedge 76. The wedge 76 is attached to a proximate pulling wire 74, with the wedge 76 between drawn between the shaft ring 72 and the pacing lead 14 when pulling wire 74 is pulled proximately in the direction of arrow 77. As indicated in FIG. 7*b* and similar to the embodiment of FIG. 6*b* described above, the pulling wire 74 may be designed to tear at a rated break point 78 under the pulling force following locking of wedge 76 or by a rotation of the pulling wire 74. FIG. 7*c* shows the wires loops 71 of the anchoring mechanism 70 in apposition with the vessel wall 12. As indicated schematically in FIGS. 7*a* and 7*b*, the anchoring mechanism 70 may be advanced over the pacing lead 14 inside a delivery catheter 75, with the wire loops initially collapsed (FIG. 7*a*). When reaching the implantation site, the delivery catheter 75 is withdrawn proximally, allowing the wire loops 31 to expand (FIG. 7*b*).

Figure 8:
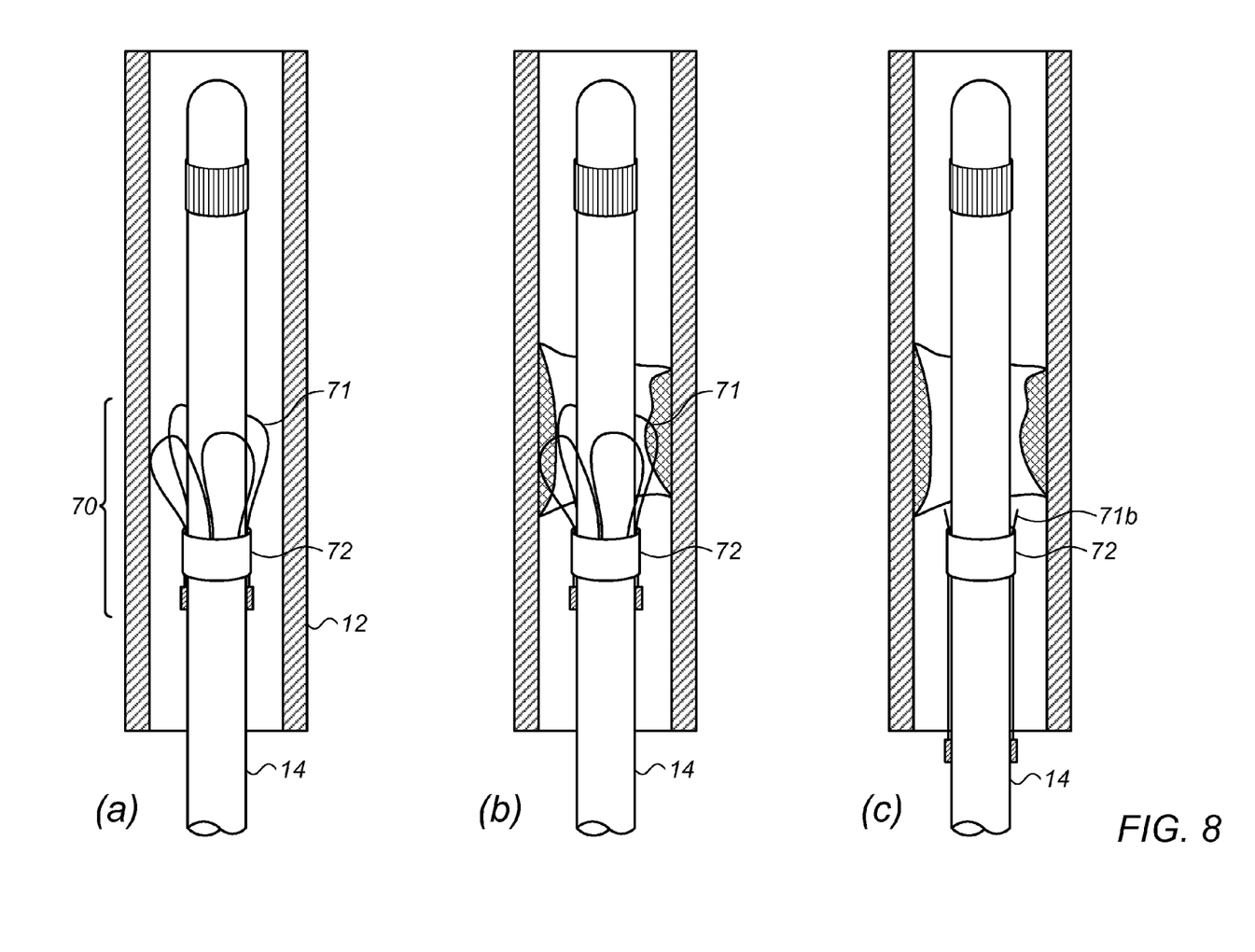
FIG. 8 depicts an approach for retrieving the anchoring mechanism of FIG. 7 in the event of tissue in-growth.

Turning now to FIG. 8, it may occasionally be necessary to retrieve the pacing lead 14 from the blood vessel 12. If the vessel wall is smooth without tissue growth, this can be accomplished, for example, by using a removal catheter which is pushed over the anchoring mechanism 70 and into which the wire loops 71 are retracted. However, retrieval becomes difficult when occlusion due to tissue growth in the wire loops prevents the use of a traditional retrieval catheter (FIG. 8*b*). In this situation, an anchoring mechanism 70 may be used where the wire loops 71 are slidingly attached to the shaft ring 72 so that they can be retracted proximally into the shaft ring 72. FIG. 8*c* and FIGS. 9*a* to 9*d* depict arrangements for pacing lead retrieval that can be used in the presence of vessel occlusion. The wire loops 71 detach from the vessel wall when pulled back toward the shaft ring 72. For example, the open wire configuration 71*b* (see also FIG. 9*a*) makes it much easier to pull the pacing wire 14 out of the tissue, because the friction resistance will be low and the vessel will not be harmed. Conversely, pulling out a closed loop shown as 71 in FIG. 8*b* may tear the tissue into which the loop 71 has grown into.

Figure 9:
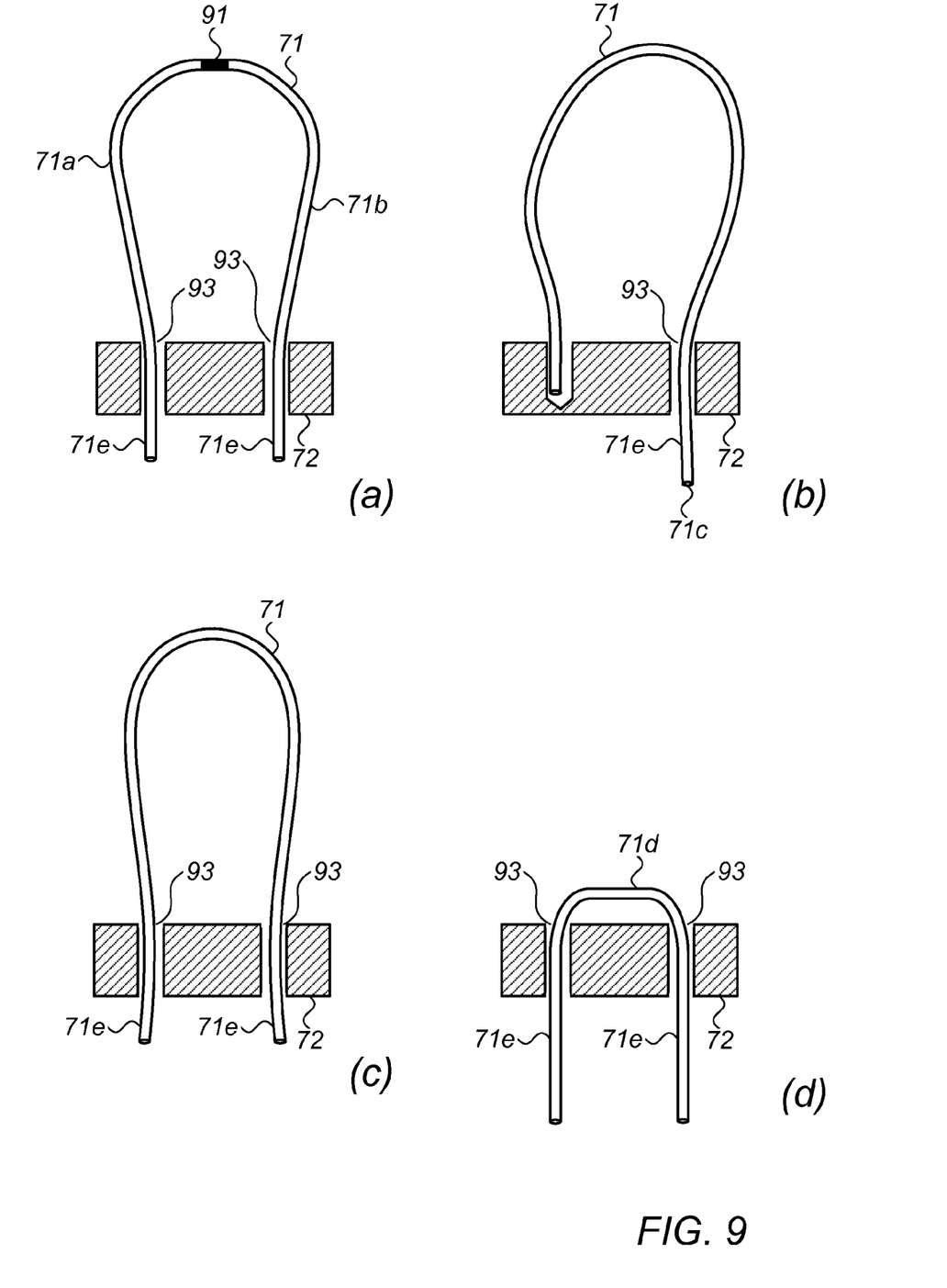
FIG. 9 shows exemplary embodiments for retracting the anchoring mechanism according to FIG. 8.

FIGS. 9*a-d* depict different embodiments of retractable wire loops 71 that can be used with the embodiment of FIG. 8*a*. In FIG. 9*a*, the wire loop 71 has a junction 91 configured to allow separation of the two wire sections 71*a* and 71*b* on either side of the junction 91. The wire sections 71*a* and 71*b* can then be separately retracted through the openings 93 in the shaft ring 32 by pulling on free ends 71*e* and removed. In FIG. 9*b*, one end 92 of the wire loop 71 is fixedly attached of the shaft ring 32, whereas the free end 71*c* of wire loop 71 can be pulled through the opening 93 in shaft ring 32 until the wire loop is collapsed. FIG. 9*c* illustrates an embodiment where the wire loop 71 can be pulled through two openings 93 in the shaft ring 72 by pulling on both free ends 71*e* until the wire loop is collapsed.

While the invention is receptive to various modifications, and alternative forms, specific examples thereof have been shown in the drawings and are herein described in detail. For example, it should be understood, that while in disclosed embodiments a tubular fixation device is advanced over the pacing lead proximate to the distal end of the pacing lead, the shape of the fixation device may also be changed into the desired deformed shape through external activation (shape memory alloys, fracture or severance of restraining elements by an external stimulus, such an electric current, magnetic forces and the like).

The implant may include any pacing lead in any vein (e.g., transvenous nerve and muscle stimulation), and may also include any sensing catheter in any vein, such as pressure sensor, flow sensor, etc. The invention is therefore not limited to the particular forms or methods disclosed, but to the contrary, the invention is meant to cover modifications, equivalents, and alternatives.

What is claimed is:

1. A fixation device for securing a wire in a body lumen, comprising:
a sleeve movable on the wire and having one or more anchoring members, said sleeve is configured to be advanced to an implant site in the body lumen in a collapsed state with a delivery catheter, wherein said anchoring member comprises a wire loop and is biased to radially expand into wall apposition in the body lumen when exiting the delivery catheter;
a securement device configured for engagement between the wire and the sleeve; and
an actuator connected to the securement device for locking the sleeve on the wire.

2. The fixation device according to claim 1, wherein the actuator is a pulling wire.

3. A fixation device for securing a wire in a body lumen, comprising:
a sleeve movable on the wire and having one or more anchoring members,
said sleeve is configured to be advanced to an implant site in the body lumen in a collapsed state with a delivery catheter, wherein said anchoring member is biased to radially expand into wall apposition in the body lumen when exiting the delivery catheter and wherein the anchoring member is retractable proximally through at least one opening in the sleeve for subsequent removal from the body lumen;
a securement device configured for engagement between the wire and the sleeve; and
an actuator connected to the securement device for locking the sleeve on the wire.

4. The fixation device according to claim 3, wherein the actuator is a pulling wire.

* * * * *